United States Patent [19]
Kohli et al.

[11] Patent Number: 4,806,068
[45] Date of Patent: Feb. 21, 1989

[54] ROTARY LINEAR ACTUATOR FOR USE IN ROBOTIC MANIPULATORS

[76] Inventors: Dilip Kohli, 16615 W. Dane Ct., Brookfield, Wis. 53005; George N. Sandor, 1717 NW. 23rd Ave., Apt. 3C, Gainesville, Fla. 32605

[21] Appl. No.: 913,523

[22] Filed: Sep. 30, 1986

[51] Int. Cl.⁴ ............................................. B66C 1/00
[52] U.S. Cl. .................................... 414/735; 74/479; 901/17; 901/22; 901/23
[58] Field of Search ...................... 901/27, 28, 29, 19, 901/22, 23, 24, 25, 50, 17; 74/469, 479; 414/735; 248/653, 654

[56] References Cited

U.S. PATENT DOCUMENTS

| | | | |
|---|---|---|---|
| 2,286,571 | 6/1942 | Polland | 901/4 X |
| 2,697,529 | 12/1954 | Hubbell et al. | |
| 3,841,499 | 10/1974 | Bullard | |
| 4,651,589 | 3/1987 | Lambert | 901/28 X |

FOREIGN PATENT DOCUMENTS

| | | | |
|---|---|---|---|
| 0127895 | 12/1984 | European Pat. Off. | |
| 2800273 | 12/1979 | Fed. Rep. of Germany | |
| 8511473 | 4/1985 | Fed. Rep. of Germany | |
| 2085185 | 12/1987 | France | 901/17 X |
| 510362 | 6/1976 | U.S.S.R. | |
| 0932017 | 5/1982 | U.S.S.R. | |
| 1049244 | 10/1983 | U.S.S.R. | |
| 1083017 | 3/1984 | U.S.S.R. | |
| 2085399 | 4/1982 | United Kingdom | |
| 8703528 | 6/1987 | World Int. Prop. O. | |

Primary Examiner—Robert J. Spar
Assistant Examiner—Jennifer L. Doyle
Attorney, Agent, or Firm—Michael, Best & Friedrich

[57] ABSTRACT

A robotic manipulator for supporting a tool or workpiece, the manipulator including at least one rotary linear actuator adapted to be supported by a base and providing for controlled movement of a manipulator link with two degrees of freedom. The robotic manipulator includes a link assembly having one end spherically joined to a movable member for supporting the movable member, the movable member being adapted to support a tool or workpiece. The link assembly is articulated, and the opposite end of the link assembly is supported by a rotary linear actuator for linear movement in a direction transverse to a longitudinal axis of the opposite end of the link assembly and for rotational movement about the axis defined by that linear movement.

22 Claims, 3 Drawing Sheets

ROTARY LINEAR ACTUATOR FOR USE IN ROBOTIC MANIPULATORS

FIELD OF THE INVENTION

The present invention relates to robotics and to actuators for use in manipulators and robots and for use in causing controlled movement of a workpiece or tool supported by a manipulator.

BACKGROUND OF THE INVENTION

Manipulators of the type commonly used in robotics applications and for supporting a workpiece or tool commonly include a plurality of articulated links joined together serially, starting with a fixed or mobile base, in end-to-end relation. A plurality of actuators are provided, one at each pivotal connection of the links, to effect movement of the links with respect to one another.

In order to produce a manipulator wherein the load or tool supported by the manipulator will be moveable with six degrees of freedom, commonly the manipulator is comprised of a plurality of links joined together in end-to-end relation, and a number of actuators are provided to produce movement of the links with respect to one another, each actuator in turn being supported by one of the links at the respective joint between links.

One of the characteristics of this arrangement is that the actuators supporting serially connected links must be capable of supporting the mass of all of the other actuators as well as the mass of the links, and the inertia experienced by one actuator will include the inertia of the links and the inertia of the actuators supported by that actuator as well as the inertia of the tool or load supported by the articulated linkage.

When such articulated linkages are used in robotics to support a tool, the position of the tool must be continually sensed. Another characteristic of the prior art manipulator linkages is that calculation of the position of a link at the end of the articulated linkage requires a sequential calculation of the relative position of each of the supporting links and actuators. A change in the position of one of the supported actuators and associated link will result in a change of the position of all of the links and actuators supported by that link. Accordingly, when the positions are calculated, the calculations must be made in sequence, first calculating the position of a base link and then serially the links supported by that first link. Because these calculations must be done in sequence, the calculation process can limit the speed of movement or operation of the manipulator and the tools supported by the manipulator.

SUMMARY OF THE INVENTION

The present invention provides an improved actuator assembly for use in a manipulator of the type used in robotics. The invention also includes an improved manipulator for use in robotics, the manipulator providing a means for supporting a workpiece or tool for movement with as many as six degrees of freedom. The manipulator can be constructed with all actuators mounted on the base, and this facilitates construction of a manipulator which can support substantially greater loads than can be supported by prior art manipulators of a similar size and weight.

More particularly, the improved actuator embodying the invention includes a robotic manipulator including a moveable member adapted to support a load or tool for selective controlled movement, and a first link means having opposite ends, one of the ends of the first link means being pivotally joined to the moveable member for supporting the moveable member, and the opposite end of the first link means including a longitudinal axis. The robotic manipulator also includes a rotary linear actuator adapted to be mounted on a base and supporting the opposite end of the first link means, the rotary linear actuator including means for supporting the opposite end of the first link means for movement in the direction of a second axis, the second axis being transverse to the longitudinal axis, and means for causing pivotal movement of the opposite end of the first link means about the second axis.

The apparatus embodying the invention also includes a rotary linear actuator for use in a robotic manipulator and which comprises a shaft having a longitudinal axis, and a rotary actuator for causing selective rotation of the shaft about the longitudinal axis. Also included is a link having opposite ends and a longitudinal axis transverse to the longitudinal axis fo the shaft. One of the opposite ends of the link includes a bore, and is supported by the shaft with the shaft housed in the bore. That end of thelink is slideable on the shaft in the direction of the longitudinal axis of the shaft, and the link is rotatable with the shaft in response to rotation of the shaft. The rotary linear actuator also includes means for causing selective linear movement of the link along the shaft in the direction of the longitudinal axis of the shaft, the means for causing linear movement including an extensible piston or jack shaft moveable in the direction of the longitudinal axis of the shaft, and means for operably connecting the piston to the end of the link.

Various features of the invention will be apparent by reference to the following description of a preferred embodiment, from the drawings and from the claims.

Figure 1:
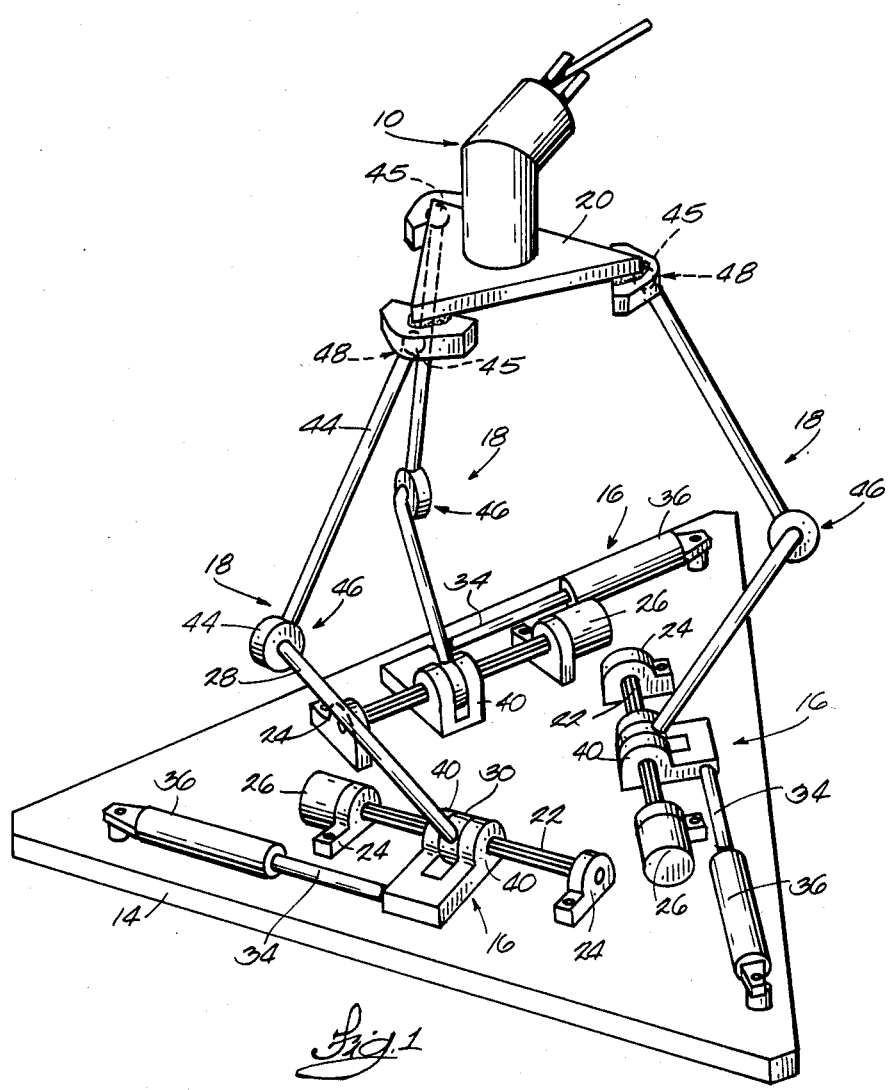
FIG. 1 is a perspective view of robotic manipulator embodying the present invention.

Before describing a preferred embodiment of the invention, it is to be understood that the invention is not limited in its application to the details of construction nor to the arrangement of the components set forth in the following description or illustrated in the drawings. The invention is capable of other embodiments and of being practiced and carried out in various ways. Also, it is to be understood that the phraseology and terminology employed herein is for the purpose of description and should not be regarded as limiting.

DESCRIPTION OF A PREFERRED EMBODIMENT

Illustrated in FIG. 1 is an apparatus embodying the invention and for use in supporting a tool 10. It will be understood by those skilled in the art that the apparatus embodying the invention could be used in many applications to support many types of loads, workpieces or tools and the illustrated tool 10 is shown merely by way of example. The apparatus includes a base 14 supporting a plurality of rotary linear actuators 16, the rotary linear actuators 16 each supporting a link assembly 18. The link assemblies 18 in turn support a platform or moveable member 20 adapted to support a load such as the tool 10.

Figure 2:
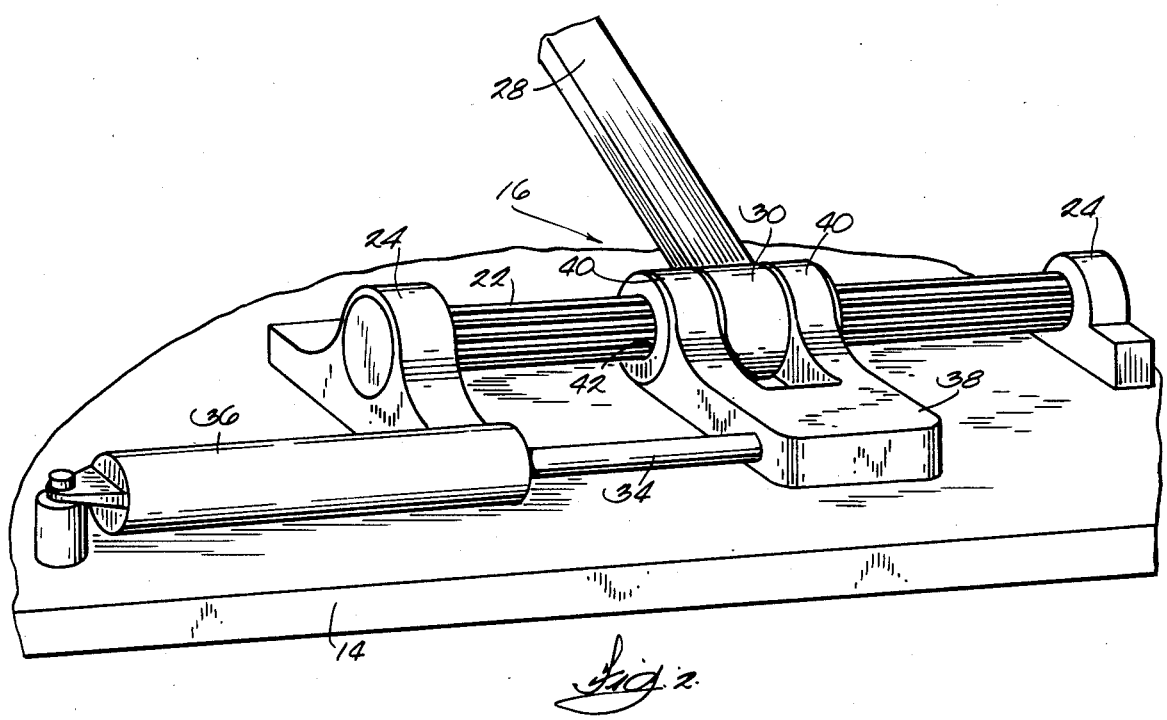
FIG. 2 is an enlarged view of a rotary-linear actuator embodied in the manipulator illustrated in FIG. 1.

The rotary linear actuators 16 are illustrated in greater detail in FIG. 2 and each includes a splined shaft 22, the shaft 22 being supported at its opposite ends by a pair of bearings 24. In the illustrated construction, the rotary linear actuators 16 are supported on the base 14 such that the longitudinal axes of the splined shafts 22 define an equilateral triangle. The bearings 24 are fixedly supported by the base 14 and in turn support the splined shafts 22 for rotation about their respective central longitudinal axes. A rotary actuator 26 is operably connected to the end of each of the splined shafts 22 to cause controlled rotation of that splined shaft about its axis. The bearings 24 supporting the splined shaft and the rotary actuator 26 are conventional and are not illustrated in detail.

The lower end of each link assembly 18 includes a first link 28 having an end member 30, the end member 30 including a central bore housing the splined shaft 22. The central bore of end member 30 has a configuration such that the end member 30 is freely slideably moveable along the length of the splined shaft 22 between the bearings 24 but such that rotation of the splined shaft 22 about its longitudinal axis will cause consequent pivotal movement of the link 28 about that longitudinal axis.

Means are also provided for causing selective slidable movement of the lower end of the link 28 along the length of the splined shaft 22. In the illustrated construction this means includes an extensible hydraulic piston 34 and cylinder 36 and a slide 38 fixed to the end of the piston rod 34. The slide 38 includes a pair of collars 40 adapted to be positioned on opposite sides of the end 30 of the link 28 to cause translational movement of the end 30 of the link 28 in response to linear movement of the piston rod 34. The piston 34 and cylinder 36 are supported by the base 14 such that their longitudinal axis is parallel to the longitudinal axis of the splined shaft 22. While the slide 38 could have various configurations, in the illustrated arrangement, the collars 40 are integrally joined together and they each include a central bore 42 having a diameter larger than the outside diameter of the splined shaft 22 such that the splined shaft 22 is freely rotatable in the bores 42 of the collars. Movement of the piston rod 34, however, is transmitted to the end 30 of the link 28 surrounding the splined shaft 22.

In the illustrated arrangement, each of the link assemblies 18 further includes a second link member 44 having one end pivotally connected by a conventional hinge joint 46 at its lower end to the upper end of the first link member 28. An upper end of the second link member 44 comprises a ball 45 and is in turn connected to the platform 20 by a ball and socket connection 48. The platform 20 includes an upper surface or supporting surface for supporting a workpiece or tool 10.

In operation of the embodiment of the invention illustrated in FIG. 1, the three cylinders 36 can cause independent movement of the lower ends 30 of each of the three links 28 along the splined shafts 22 in the direction of the longitudinal axis of those shafts. The rotary actuators 26 can similarly cause independent rotation of the splined shafts 22 and consequent pivotal movement of the links 28 about the axes of the splined shafts 22.

It will be appreciated by those skilled in the art that such independent movement of the lower ends of the three links 28 will result in a consequent movement of the platform 20, and that such movement of the platform can comprise movement with six degrees of freedom. For example, if the platform 20 supports a tool 10 comprising a means for gripping a workpiece, proper actuation of the three rotary linear actuators 16 can first cause movement of the platform to a first selected position wherein the tool 10 can grip the workpiece. Subsequent actuation of the three rotary lniear actuators can then cause movement of the platform and delivery of the workpiece to a second selected position. Because the platform is supported for movement through six degrees of freedom, the workpiece can be engaged and delivered at any selected position within the range of movement of the link assemblies 18 supporting the platform.

One of the principal advantages of the construction illustrated in FIG. 1 is that the supporting platform 20 can be provided with movement through six degrees of freedom while all of the rotary-linear actuators 16 can be fixed to the base 14. Because all of the actuators can be supported by the base, and because the link assemblies 18 are not connected together serially in end-to-end relation, and with the actuators supported serially by the links, the mass of the actuators is not supported by the links. Accordingly, the strength of the links 18 and the force exerted by the actuators 16 functions to support and move the platform 20 and the workpiece supported by the platform, and is not used to support a plurality of links and actuators connected in end-to-end relation of serially. Since the mass of the actuators 16 need not be controlled, use of conventional off-the-shelf rotary actuators 26 and pistons and cylinder assemblies is permissible.

Another important feature in the construction of a robotic manipulator for supporting a tool is in connection with providing an arrangement wherein the position of the tool can be conveniently rapidly calculated such that the actuators can be properly controlled to provide for accurate control of the position of the tool. If the links and actuators are connected serially such that the links are connected in end-to-end relation with actuators, calculation of the position of alink at an end of a serial assembly of links first requires calculation of the position of all of the one or more actuators supporting that link. Since, in the manipulator configuration embodying the invention and illustrated in FIG. 1, the links and actuators are not connected serially, the calculation of the position of a link supported by one actuator does not further require the sequential calculation of the relative position of additional actuators in turn supporting that one actuator.

Figure 3:
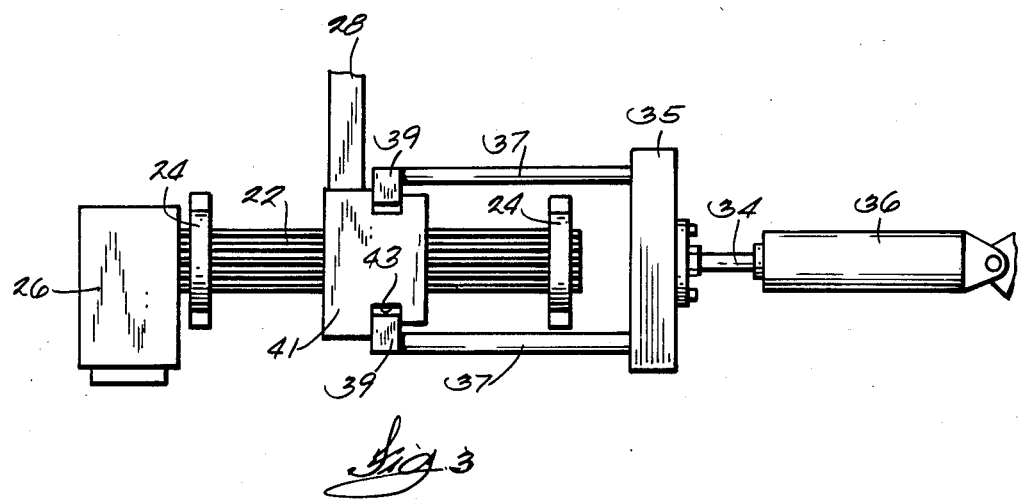
FIG. 3 is a view similar to FIG. 2 and showing a rotarylinear actuator including an alternative construction.

Illustrated in FIG. 3 is an alternative embodiment of a rotary linear actuator embodying the invention. In the rotary linear actuator construction shown in FIG. 2 the link 28 is rotatable through an arc of less than 360° since the bracket 38 can interfere with rotation of the link 28. The arrangement shown in FIG. 3 illustrates apparatus similar to that shown in FIG. 2 but wherein the link 28 is freely rotatable around the axis of the splined shaft 22.

More particularly, in the construction shown in FIG. 3, a splined shaft 22 is supported at its opposite ends by a pair of bearings 24 and a conventional rotary actuator 26 is provided for causing selective controlled rotation of the splined shaft 22. A piston rod 34 and cylinder 36 are mounted such that the extension of the piston rod 34 is parallel to the axis of rotation of the splined shaft 22. The piston rod 34 supports a cross bar 35, and a pair of spaced apart parallel rods 37 extend from the cross bar 35 and are positioned on opposite sides of the splined shaft 22. The rods 37 each include a projecting end supporting a ring 39.

The link 28 is fixedly supported by a hub or slide member 41 supported on the splined shaft 22 for slideable movement along the length of the splined shaft and for rotation with the splined shaft. The hub 41 includes a peripheral groove 43 housing a radially inward portion of the ring 39. The groove 43 houses the ring 39 such that the hub 41 and link 28 are freely rotatable about the axis of the splined shaft but wherein extension or retraction of the piston rod 34 and consequent movement of the ring 39 will result in translation of the collar 41 and the link 28 along the length of the splined shaft 22. In operation of the rotary-linear actuator illustrated in FIG. 3, the link is rotatable fully 360°.

Figure 4:
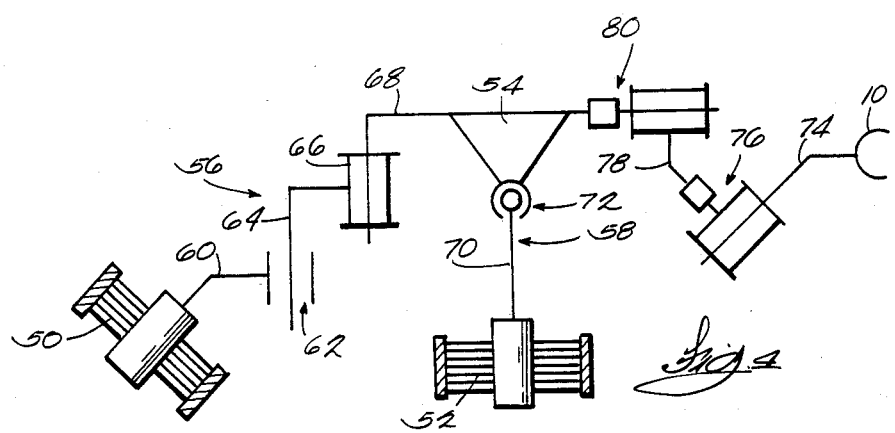
FIG. 4 is a schematic view of a robotic manipulator comprising an alternative embodiment of the invention.

Illustrated schematically in FIG. 4 is an alternative embodiment of a robotic manipulator employing a pair of rotary linear actuators of the type illustrated in FIGS. 2 and 3 and embodying the invention. In the arrangement shown in FIG. 4 a pair of rotary linear actuators 50 and 52 are fixedly supported by a base 14, the rotary linear actuators 50 and 52 each having a construction like those illustrated in FIGS. 1 and 2. The apparatus shown in FIG. 4 also includes a platform 54 supported by a pair of link assemblies 56 and 58. The first link assembly 56 includes a first link 60 having one end supported by the rotary linear actuator 50 and an opposite end connected by a cylindric hinge assembly or cylindric pair 62 to an end of a second link 64. The cylindric hinge assembly 62 permits relative hinged movement of the links 60 and 64 with respect to one another and longitudinal movement of the second link 64 in the direction of the axis of rotation of the hinge assembly 62 with respect to the other link member 60. The opposite end of second link 64 is connected by a hinge 66 to a third link 68, the third link 68 being fixed to the platform 54. The cylindric hinge assembly 62 and the hinge 66 are of the type commonly used in robotic manipulators and are illustrated only schematically.

In the embodiment illustrated in FIG. 4, the second link assembly 58 comprises a link 70 having one end fixed to the rotary linear actuator 52 and an opposite end connected by a ball and socket connection 72 to the platform 54.

The manipulator illustrated in FIG. 4 further includes a tool 10 supported by a link 74, the link 74 in turn being supported by a rotary actuator 76. The link 74 has a longitudinal axis, and the rotary actuator 76 causes selective rotation of the link 74 about the longitudinal axis. The rotary actuator 76 is in turn supported by a link 78, the link 78 being supported by a second rotary actuator 80. The rotary actuator 80 is supported by the platform 54. The rotary actuators 76 and 80 are conventional rotary actuators of the type commonly used in robotic manipulators and are not illustrated other than schematically.

It will be understood by those skilled in the art that the robotic manipulator illustrated in FIG. 4 supports the tool 10 such that the tool can move with six degrees of freedom. The platform 54 is supported by the two rotary linear actuators 50 and 52 for movement with four (4) degrees of freedom, and the two rotary actuators 80 and 76 supported by the platform 54 provide the tool with two (2) additional degrees of freedom.

FIGS. 5-14 illustrate a plurality of additional robotic manipulator constructions employing a rotary linear actuator 82 embodying the invention, the manipulators each supporting a platform 84 for movement with three (3) degrees of freedom. The platform 84 can be used, in turn, to support a conventional robotic wrist (not shown) for supporting a tool or workpiece and providing an additional three (3) degrees of freedom.

Figure 5:
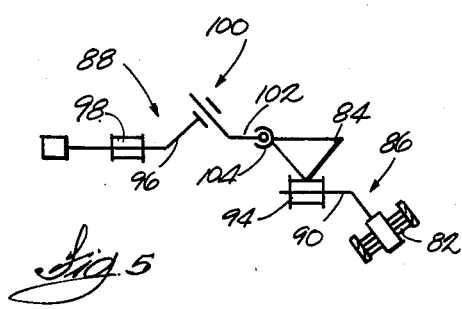
FIGS. 5–14 are schematic views of robotic manipulators comprising alternative embodiments of the invention.

Referring more specifically to the robotic manipulator illustrated in FIG. 5, the platform 84 is supported by a pair of link assemblies 86 and 88, link assembly 86 comprising a link 90 having one end supported by a rotary linear actuator 82 of the type illustrated in either FIG. 2 or FIG. 3. An opposite end of link 90 is connected by a hinge 94 to one side of the platform 84. The other link assembly 88 comprises a first link 96 having one end supported by a rotary actuator 98. An opposite end of that link 96 is connected by a cylindric hinge assembly 100 to a second link 102. The cylindric hinge assembly 100 is conventional and provides for rotation of the second link 102 about its longitudinal axis with respect to the first link 96 as well as linear sliding movement of the second link 102 in the direction of its longitudinal axis with respect to the first link 96. An opposite end of the second link 102 is connected by a ball and socket 104 to the platform 84. This arrangement supports the platform 84 for controlled movement with three (3) degrees of freedom.

Figure 6:
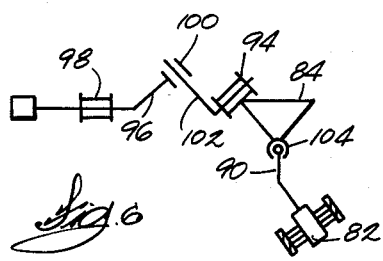

FIG. 6 illustrates an alternative arrangement of the structure shown in FIG. 5 wherein the link 90 is connected to the platform 84 by a ball and socket connection 104, and the second link 102 is connected to the platform 84 by a hinge 94.

Figure 7:
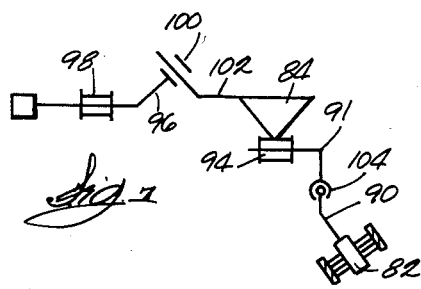

FIG. 7 illustrates an embodiment of the invention similar to that shown in FIGS. 5-6 but wherein the second link assembly 88 has an end fixed to the platform 84. Additionally, the first link assembly 86 is comprised of a pair of links 90 and 91 joined together serially by a ball and socket connection 104. The first link 90 has an end supported by the rotary linear actuator 82 and an opposite end connected by the ball and socket 104 to the second link 91. The opposite end of the second link 91 is connected by a hinge 94 to the platform 84.

Figure 8:
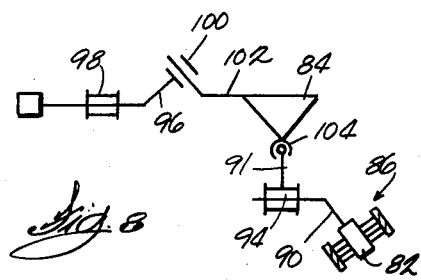

FIG. 8 illustrates a robotic manipulator similar to that shown in FIG. 7 but wherein the first and second links 90 and 91, respectively, of the first link assembly 86 are joined by a hinge 94, and the second link 91 is connected to the platform 84 by a ball and socket assembly 104.

Figure 9:
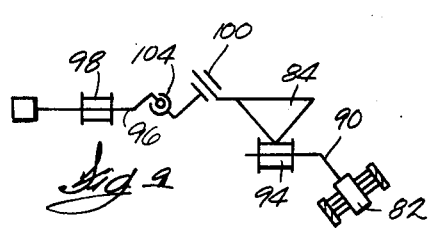

FIG. 9 illustrates a robotic manipulator assembly similar to that shown in FIG. 5 but wherein the link 90 of the first link assembly 86 is connected to the platform 84 by a hinge 94 and the first and second link 96 and 102 of the second hinge assembly 88 are connected by a ball and socket assembly 104.

Figure 10:
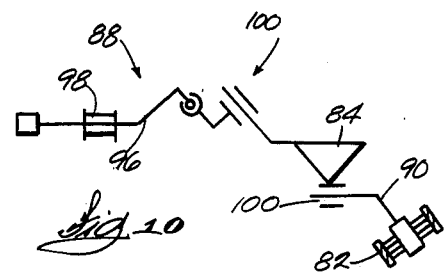

FIG. 10 illustrates a robotic manipulator similar to those shown in FIGS. 5-9 wherein the link 90 supported by the rotary linear actuator 82 and an opposite end is connected to the platform by a cylindric pair 100.

Figure 11:
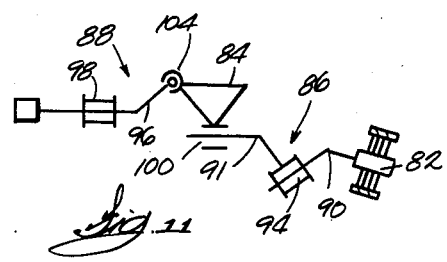

FIG. 11 illustrates a robotic manipulator assembly like those shown in FIGS. 5-10 wherein the first link assembly 86 is comprised of a first link 90 supported by a rotary linear actuator 82 and a second link 91 connected to the platform 84 by a cylindric pair 100. The first and second links 90 and 91 are joined by a hinge 94. The second link assembly 88 is comprised of a link 96 having one end supported by a rotary actuaror 98 and an opposite end connected by a ball and socket 104 to the platform 84.

Figure 12:
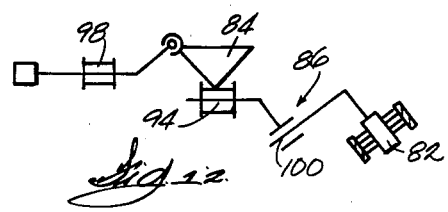

FIG. 12 illustrates a robotic manipulator embodying the invention and similar to the arrangement shown in FIG. 11 but wherein the positions of the hinge 94 and the cyclindric pair 100 in the first link assembly 86 are interchanged.

Figure 13:
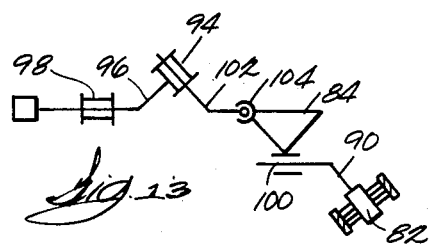

FIG. 13 illustrates a robotic manipulator similar to that shown in FIG. 5 but wherein the link 90 is connected to the platform 84 by a cylindric pair 100, and wherein the first and second links 96 and 102 of second link assembly 88 are joined by a hinge 94.

Figure 14:
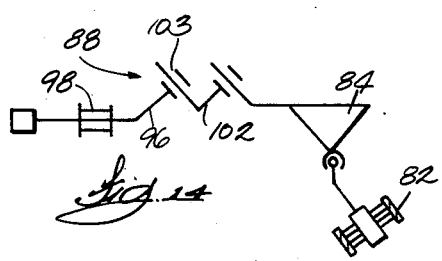

FIG. 14 illustrates a robotic manipulator similar to that shown in FIG. 6 but wherein the second link 102 of the second link assembly 88 is connected to the platform 85 by a first cylindric pair 100 and is joined to the first link 96 by a second cylindric pair 103.

Various features of the invention are set forth in the following claims.

We claim:

1. A robotic manipulator adapted to be supported by a base and for supporting a load for selective controlled movement, the robotic manipulator comprising:
a movable member adapted to support a load for selective controlled movement,
a first link means having opposite ends, one of said ends of said first link means being movably joined to said movable member for supporting said movable member, and the opposite end of said first link means including a longitudinal axis,
a rotary linear actuator adapted to be supported by the base and supporting the opposite end of said first link means, said rotary linear actuator including means for supporting said opposite end of said first link means for movement in the direction of a second axis, said second axis being transverse to said longitudinal axis, means for causing linear movement of said opposite end of said first link means in the direction of the second axis, the means for causing linear movement of the opposite end of the first link means being adapted to be supported by the base and means for causing pivotal movement of said opposite end of said first link means about said second axis, the means for causing pivotal movement of said opposite end of the first link means being adapted to be supported by the base independently of the means for causing linear movement of the opposite end of the first link means.

2. A robotic manipulator as set forth in claim 1 wherein said first link means comprises a first link having opposite ends, one of said opposite ends of said first link being movably joined to said movable member, and a second link, said second link having one end supported by said rotary linear actuator and an opposite end movably connected to the other of the opposite ends of said first link for supporting said first link.

3. A robotic maniuiplator as set forth in claim 1 and further including a second link means having opposite ends, said second link means having one end movably connected to said movable member and spaced from said one end of said first link means, and the opposite end of said second link means including a second longitudinal axis, and a second rotary linear actuator adapted to be supported by the base and for supporting the opposite end of said second link means, said second rotary linear actuator including means for supporting said opposite end of said second link means for movement in the direction of a third axis, said third axis being transverse to said longitudinal axis of said opposite end of said second link means, means for causing selective movement of said opposite end of said second link means in the direction of the third axis, the means for causing selective movement of said opposite end of said second link means being adapted to be supported by the base, and means for causing pivotal movement of said opposite end of said second link means about said third axis, the means for causing pivotal movement of said opposite end of said second link means being adapted to be supported by the base independently of the means for causing selective movement of the opposite end of the second link means.

4. A robotic manipulator as set forth in claim 3 and further including a third link means having opposite ends, said third link means having one end movably connected to said movable member and spaced from said one end of said first link means and said one end of said second link means, and the opposite end of the said third link means including a longitudinal axis, and a third rotary linear actuator adapted to be supported by the base and for supporting the opposite end of the third link means, said third rotary linear actuator including means for supporting said opposite end of said third link means for movement in the direction of a fourth axis transverse to said longitudinal axis of said opposite end of said third link means, means for causing selective movement of said opposite end of said third link means in the direction of the fourth axis, and means for causing pivotal movement of said opposite end of said third link means about said fourth axis.

5. A robotic manipulator as set forth in claim 1 wherein said means for supporting siad opposite end of said link includes a shaft having a longitudinal axis comprising said second axis, wherein said opposite end of said first link assembly includes a bore housing said shaft, said opposite end of said first link assembly being supported on said shaft for movement along the length of said shaft, and said opposite end of said link assembly being rotatably fixed to said shaft for rotation with said shaft, and wherein said means for causing linear movement includes means for causing linear movement of said opposite end of said first link assembly along the length of said shaft.

6. A robotic manipulator as set forth in claim 5 wherein said means for causing linear movement of said opposite end of said first link includes a cylinder adapted to be supported by the base independently of said means for causing pivotal movement and an extensible piston rod housed in said cylinder and means for operably connecting said piston rod to said opposite end of said link assembly to cause movement of said opposite end of said link assembly in the direction of said second axis in response to movement of said extensible piston rod.

7. A robotic manipulator as set forth in claim 6 wherein said means for causing pivotal movement of said opposite end of said link assembly includes a rotary actuator adapted to be supported by the base and connected to said shaft for causing selective rotation movement of said shaft.

8. A rotary linear actuator for use in a robotic manipulator, the rotary linear actuator being adapted to be supported by a base and comprising:
a shaft having a longitudinal axis, and said shaft having opposite ends means for causing selective rotation of said shaft about said longitudinal axis, said means for causing selective rotation being adapted to be supported by the base, a link including opposite ends and a longitudinal axis transverse to said longitudinal axis of said shaft, one of said opposite ends of said link including a bore, said one of said opposite ends of said link being supported by said shaft with said shaft housed in said bore, said one of said ends of said link being slidable on said shaft in the direction of said longitudinal axis of said shaft, and said link being rotatable with said shaft in response to rotation of said shaft, and means for causing selective linear movement of said link along said shaft in the direction of said longitudinal axis of said shaft, said means for causing linear movement including an extensible piston rod moveable in the direction of said longitudinal axis of said shaft, and means for operably connecting said extensible piston rod to said end of said link, and said means for causing selective linear movement of said link along the shaft being adapted to be supported by the base independently of said means for causing selective rotation of said shaft.

9. Apparatus as set forth in claim 8 wherein said means for connecting said piston to said link includes a slide member fixed to said piston rod for movement with said piston rod, said slide member including a first member engageable with one side of said link and a second member engageable with an opposite side of said link.

10. Apparatus as set forth in claim 8 wherein said shaft is a splined shaft and wherein said one of said opposite ends of said link is supported on said splined shaft for slideable movement along the length of said splined shaft.

11. Apparatus as set forth in claim 8 whrein said means for causing selective rotation of said shaft includes a rotary actuator operably connected to said shaft.

12. A robotic manipulator adapted to be supported by a base and for supporting a load for selective controlled movement, the robotic manipulator comprising:

a movable member adapted to support a load for selective controlled movement, a first link means having opposite ends, one of said ends of said first link means being movably joined to said movable member for supporting said movable member, and the opposite end of said first link means including a longitudinal axis, a first rotary linear actuator adapted to be supported by the base and supporting the opposite end of said first link means, said rotary linear actuator including means for supporting said opposite end of said first link means for movement in the direction of a second axis, said second axis being transverse to said longitudinal axis, means for causing linear movement of said opposite end of said first link means in the direction of said second axis, the means for causing linear movement of said opposite end of said first link means being adapted to be supported by the base, and means for causing pivotal movement of said opposite end of said first link means about said second axis, the means for causing pivotal movement being adapted to be supported by the base independently of the means for causing linear movement of the opposite end of the first link means, a second link means having opposite ends, said second link means including a first link connected to said movable member for supporting said movable member, a second link supporting said first link, means for joining said second link and said first link, a third link supporting said second link, means for operably joining said second link to said third link such that said second link is translationally movable with respect to said third link, said third link having a second longitudinal axis, and a second rotary linear actuator adapted to be supported by the base and for supporting the third link, said second rotary linear actuator including means for supporting said third link for movement in the direction of a third axis, said third axis being transverse to said longitudinal axis of said third link, means for causing linear movement of said third link in the direction of a third axis, the means for causing linear movement of said third link being adapted to be supported by the base, and means for causing pivotal movement of said third link about said third axis said means for causing pivotal movement of said third link being adapted to be supported by the base independently of the means for causing linear movement of the third link.

13. A robotic manipulator adapted to be supported by a base and for supporting a load for selective controlled movement, the robotic manipulator comprising:

a movable member adapted to support a load for selective controlled movement, a first link means having opposite ends, one of said opposite ends being connected to said movable member for supporting said movable member, and the other of the opposite ends of said first link means having a longitudinal axis, a rotary linear actuator adapted to be supported by the base and supporting the other of said opposite ends of said first link means, said rotary linear actuator including means for supporting said opposite end of said first link means for movement in the direction of a second axis, said second axis being transverse to said longitudinal axis, means for causing linear movement of said opposite end of the first link means in the direction of said second axis, and means for causing pivotal movement of said opposite ends of said first link means about said second axis, a second link means having opposite ends, one of said ends of said second link means supporting said movable member, and the other of said opposite ends having a longitudinal axis, and a rotary actuator for causing selective rotation of said other of said opposite ends of said second link means for rotation about said longitudinal axis of said opposite end of said second link means.

14. A robotic manipulator adapted to be supported by a base and for supporting a load for selective controlled movement, the robotic manipulator comprising:

a movable member adapted to support a load for selective controlled movement, a first link means having opposite ends, one of said ends of said fist link means being movably joined to said movable member for supporting said movable member, and the opposite end of said first link means including a longitudinal axis, a rotary linear actuator adapted to be supported by the base and supporting the opposite end of said first link means, said rotary linear actuator including means for supporting said opposite end of said first link means for movement in the direction of a second axis, said second axis being transverse to said longitudinal axis and means for causing pivotal movement of said opposite end of said first link means about said second axis, said means for causing pivotal movement of said opposite end of said first link means being adapted to be supported by the base, said means for supporting said opposite end of said first link means including a shaft having a longitudinal axis comprising said second axis, wherein said opposite end of said first link assembly includes a bore housing said shaft, said opposite end of said first link assembly being supported on said shaft for movement along the length of said shaft, and said opposite end of said first link means being rotatably fixed to sid shaft for rotation with said shaft, and wherein said rotary linear actuator further includes means for causing linear movement of said opposite end of said fist link assembly along the length of said shaft, said means for causing linear movement being adapted to be supported by the base independently of said means for causing pivotal movement.

15. A robotic manipulator as set forth in claim 14 wherein said means for causing linear movement of said opposite end of said first link includes a cylinder and an extensible piston rod housed in said cylinder and means for operably connecting said piston rod to said opposite end of said link assembly to cause movement of said opposite end of said link assembly in the direction of said second axis in response to movement of said extensible piston rod.

16. A robotic manipulator as set forth in claim 15 wherein said means for causing pivotal movement of said opposite end of said link assembly includes a rotary actuator connected to said shaft for causing selective rotation movement of said shaft.

17. A robotic manipulator as set forth in claim 1 wherein said one of said ends of said first link means is joined to said movable member by a ball and socket connection to provide a spherical joint between first link means and movable member.

18. A rotary linear actuator for use in a robotic manipulator, the rotary linear actuator comprising:

a shaft having a longitudinal axis, and said shaft having opposite ends means for causing selective rotation of said shaft about said longitudinal axis, a link including opposite ends and a longitudinal axis transverse to said longitudinal axis of said shaft, one of said opposite ends of said link including a bore, said one of said opposite ends of said link being supported by said shaft with said shaft housed in said bore, said one of said ends of said link being slideable on said shaft in the direction of said longitudinal axis of said shaft, and said link being rotatable with said shaft in response to rotation of said shaft, and means for causing selective linear movement of said link along said shaft in the direction of said longitudinal axis of said shaft, said means for causing linear movement including an extensible piston rod moveable in the direction of said longitudinal axis of said shaft, and means for operably connecting said piston to said end of said link, said means for connecting said piston to said link including a slide member fixed to said piston rod for movement with said piston rod, said slide member including a first member engageable with one side of said link and a second member engageable with an opposite side of said link.

19. A rotary linear actuator for use in a robotic manipulator, the rotary linear actuator comprising:

a shaft having a longitudinal axis, and said shaft having opposite ends means for causing selective rotation of said shaft about said longitudinal axis, a link including opposite ends and a longitudinal axis transverse to said longitudinal axis of said shaft, one of said opposite ends of said link including a bore, said one of said opposite ends of said link being supported by said shaft with said shaft housed in said bore, said one of said ends of said link being slideable on said shaft in the direction of said longitudinal axis of said shaft, and said link being rotatable with said shaft in response to rotation of said shaft, and means for causing selective linear movement of said link along said shaft in the direction of said longitudinal axis of said shaft, said means for causing linear movement including an extensible piston rod moveable in the direction of said longitudinal axis of said shaft, and means for operably connecting said piston to said end of said link, said shaft being a splined shaft and said one of said opposite ends of said link being supported on said splined shaft for slideable movement along the length of said splined shaft.

20. A robotic manipulator adapted to be supported by a base and for supporting a load for selective controlled movement, the robotic manipulator comprising:

a movable member adapted to support a load for selective controlled movement, a first link means having opposite ends, one of said ends of said first link means being movably joined to said movable member for supporting said movable member, and the opposite end of said first link means including a longitudinal axis, a rotary linear actuator adapted to be supported by the base and supporting the opposite end of said first link means, said rotary linear actuator including means for supporting said opposite end of said first link means for movement in the direction of a second axis, said second axis being transverse to said longitudinal axis, means for causing linear movement of said opposite end of said first link means in the direction of the second axis and means for causing pivotal movement of said opposite end of said first link means about said second axis a second link means having opposite ends, said second link means having one end movably connected to said movable member and spaced from said one end of said first link means, and the opposite end of said second link means including a second longitudinal axis, and a second rotary linear actuator adapted to be supported by the base and for supporting the opposite end of said second link means, said second rotary linear actuator including means for supporting said opposite end of said second link means for movement in the direction of a third axis, said third axis being transverse to said longitudinal axis of said opposite end of said second link means, means for causing selective movement of said opposite end of said second link means in the direction of the third axis, and means for causing pivotal movement of said opposite end of said second link means about said third axis, said third axis defining an angle with respect to said second axis.

21. A robotic manipulator as set forth in claim 20 and further including a third link means having opposite ends, said third link means having one end movably connected to said movable member and spaced from said one end of said first link means and said one end of said second link means, and the opposite end of the said third link means including a longitudinal axis, and a third rotary linear actuator adapted to be supported by the base and for supporting the opposite end of the third link means, said third rotary linear actuator including means for supporting said opposite end of said third link means for movement in the direction of a fourth axis transverse to said longitudinal axis of said opposite end of said third link means, means for causing selective movement of said opposite end of said third link means in the direction of the fourth axis, and means for causing pivotal movement of said opposite end of said third link means about said fourth axis, said fourth axis defining an angle with respect to said second axis and defining an angle with respect to said third axis.

22. A robotic manipulator adapted to be supported by a base and for supporting a load for selective controlled movement, the robotic manipulator comprising:
   a moveable member adapted to support a load for selective controlled movement,
   a first link means having opposite ends, one of said ends of said first link means being pivotally joined to said moveable member for supporting said moveable member, and the opposite end of said first link means including a longitudinal axis,
   a rotary linear actuator adapted to be supported by the base and supporting the opposite end of said first link means, said rotary linear actuator including means for supporting said opposite end of said first link means for movement in the direction of a second axis, said second axis being transverse to said longitudinal axis, and means for causing pivotal movement of said opposite end of said first link means about said second axis,
   a second link means having opposite ends, said second link means including a first link connected to said moveable member for supporting said moveable member, a second link supporting said first link, means for joining said second link and said first link, a third link supporting said second link, means for operably joining said second link to said third link such that said second link is translationally moveable with respect to said third link, said third link having a second longitudinal axis, and
   a second rotary linear actuator adapted to be supported by the base and for supporting the third link, said second rotary linear actuator including means for supporting said third link for movement in the direction of a third axis, said third axis being transverse to said longitudinal axis of said third link, and means for causing pivotal movement of said third link about said third axis, and said third axis defining an angle with respect to said second axis.

* * * * *